US00PP20323P2

(12) United States Plant Patent
Schweizer

(10) Patent No.: US PP20,323 P2
(45) Date of Patent: Sep. 15, 2009

(54) ***DIANTHUS* PLANT NAMED 'HEART'S DESIRE'**

(50) Latin Name: *Dianthus hybrida*
Varietal Denomination: Heart's Desire

(75) Inventor: Pamela S. Schweizer, Lancaster, PA (US)

(73) Assignee: Board of Regents of University of Nebraska, Lincoln, NE (US)

( * ) Notice: Subject to any disclaimer, the term of this patent is extended or adjusted under 35 U.S.C. 154(b) by 0 days.

(21) Appl. No.: 12/218,286

(22) Filed: Jul. 14, 2008

(51) Int. Cl.
*A01H 5/00* (2006.01)

(52) U.S. Cl. ..... Plt./272

(58) Field of Classification Search ..... Plt./272
See application file for complete search history.

*Primary Examiner*—Kent L Bell
(74) *Attorney, Agent, or Firm*—C. A. Whealy

(57) ABSTRACT

A new and distinct cultivar of *Dianthus* plant named 'Heart's Desire', characterized by its compact, upright and uniformly mounded plant habit; vigorous growth habit; short internodes and freely branching habit; dense and bushy growth habit; numerous pink and red purple bi-colored flowers that are positioned above and beyond the foliage; and excellent garden performance.

1 Drawing Sheet

Botanical designation: *Dianthus hyhrida.*
Cultivar denomination: 'Heart's Desire'.

BACKGROUND OF THE INVENTION

The present invention relates to a new and distinct cultivar of *Dianthus* plant, botanically known as *Dianthus hybrida,* grown as a container and garden plant, and hereinafter referred to by the name 'Heart's Desire'.

The new *Dianthus* is a naturally-occurring whole plant mutation of *Dianthus hybrida* 'Rosish One', not patented. The new *Dianthus* was discovered and selected by the Inventor as a single plant from within a population of plants of 'Rosish One' in a controlled greenhouse environment in Smoketown, Pa. on Jun. 1, 2005.

Asexual reproduction of the new cultivar by vegetative cuttings propagated in a controlled greenhouse environment in Smoketown, Pa. since Oct. 1, 2005, has shown that the unique features of this new *Dianthus* are stable and reproduced true to type in successive generations of asexual reproduction.

SUMMARY OF THE INVENTION

Plants of the new *Dianthus* have not been observed under all possible environmental conditions. The phenotype may vary somewhat with variations in environment such as temperature and light intensity, without, however, any variance in genotype.

The following traits have been repeatedly observed and are determined to be the unique characteristics of 'Heart's Desire'. These characteristics in combination distinguish 'Hearts's Desire' as a new and distinct cultivar of *Dianthus:*

1. Compact, upright and uniformly mounded plant habit.
2. Vigorous growth habit.
3. Short internodes and freely branching habit; dense and bushy growth habit.

4. Numerous pink and red purple bi-colored flowers that are positioned above and beyond the foliage.
5. Excellent garden performance.

Plants of the new *Dianthus* differ from plants of the parent, 'Rosish One' primarily in flower form as plants of the new *Dianthus* have flatter and more open flowers than plants of 'Rosish One'. In addition, plants of the new *Dianthus* and 'Rosish One' differ in flower color as plants of 'Rosish One' have dark pink-colored flowers with white-colored margins.

Plants of the new *Dianthus* can also be compared to plants of *Dianthus* 'Pixie', disclosed in U.S. Plant Pat. No. 13,578. Plants of the new *Dianthus* differ from plants of 'Pixie' in the following characteristics:

1. Plants of the new *Dianthus* are more upright and more uniformly mounded than plants of 'Pixie'.
2. Plants of the new *Dianthus* and 'Pixie' differ in flower color as plants of 'Pixie' have red purple-colored flowers with lighter red purple spots and margins.

BRIEF DESCRIPTION OF THE PHOTOGRAPHS

The accompanying photographs illustrate the overall appearance of the new *Dianthus.* These photographs show the colors as true as it is reasonably possible to obtain in colored reproductions of this type. Colors in the photographs may differ slightly from the color values cited in the detailed botanical description which accurately describe the colors of the new *Dianthus.*

The photograph at the bottom of the sheet comprises a side perspective view of a typical flowering plant of 'Heart's Desire' grown in a container.

The photograph at the top of the sheet is a close-up view of typical flowers of 'Heart's Desire'.

DETAILED BOTANICAL DESCRIPTION

In the following description, color references are made to The Royal Horticultural Society Colour Chart, 1995 Edition, except where general terms of ordinary dictionary significance are used. Measurements and numerical values represent averages for typical flowering plants. The aforementioned photographs and following observations and measurements describe plants grown during the spring in Lancaster, Pa. in a polyethylene-covered greenhouse and under conditions and practices which approximate those generally used in commercial *Dianthus* production. During the production of the plants, day temperatures ranged from 16° C. to 29° C. and night temperatures averaged 16° C. Plants were pinched one time and were seven months from planting when the photographs and the detailed description were taken.

Botanical classification: *Dianthus hybrida* 'Heart's Desire'.

Parentage: Naturally-occurring whole plant mutation of *Dianthus hybrida* 'Rosish One', not patented.

Propagation:

*Type.*—Terminal vegetative cuttings.

*Time to initiate roots, summer.*—About seven days at 28° C.

*Time to initiate roots, winter.*—About ten days at 28° C.

*Time to produce a rooted young plant, summer.*—About 18 to 20 days at 28° C.

*Time to produce a rooted young plant, winter.*—About 22 days at 21° C.

*Root description.*—Thin, fleshy; white in color.

*Rooting habit.*—Freely branching; moderately dense.

Plant description:

*Plant form.*—Compact, upright and uniformly mounded plant habit.

*Growth and branching habit.*—Vigorous and freely-branching growth habit with about 12 to 14 lateral branches, pinching enhances lateral branch development; relatively short internodes; dense and bushy growth habit.

*Plant height.*—About 16.5 cm.

*Plant diameter or spread.*—About 26 cm.

*Lateral branches.*—Length About 15 cm. Diameter: About 3 mm. Internode length: About 5 mm. Texture: Smooth, glabrous. Color: Close to 145C.

*Leaf description.*—Arrangement: Decussate, simple; sessile. Length: About 5.4 cm. Width: About 3 mm. Shape: Acicular. Apex: Acute. Base: Truncate; decurrent. Margin: Entire. Texture, upper surface: Smooth, glabrous with silvery-blue bloom. Texture, lower surface: Smooth, glabrous. Venation pattern: Parallel. Color: Developing leaves, upper and lower surfaces: Close to 147B. Fully expanded leaves, upper surface: Close to 189A; midvein, close to 189A. Fully expanded leaves, lower surface: Close to 191A; midvein, close to 191A.

Flower description:

*Flower type and habit.*—Rotate, flat, mostly open, terminal and axillary flowers. Flowers positioned above and beyond the foliage; flowers typically face upright to outwardly. Flowers faintly fragrant; spicy, clove-like.

*Natural flowering season.*—Flowering is continuous during the spring in Pennsylvania.

*Flower longevity.*—On the plant, flowers maintain good substance and color for about ten days; flowers persistent.

*Flower diameter.*—About 3.3 cm.

*Flower depth.*—About 3.2 cm.

*Flower buds.*—Length: About 2.7 cm. Diameter: About 8 mm. Shape: Oblong. Color: Close to 155A.

*Petals.*—Quantity/arrangement: About 20 in about four to five whorls. Length: About 3.2 cm. Width: About 1.4 cm. Shape: Roughly spatulate. Apex: Emarginate; lacerate. Base: Attenuate. Margin: Lacerate, ragged. Texture, upper surface: Smooth, glabrous; towards the base, pubescent. Texture, lower surface: Smooth, glabrous. Color: When opening, upper surface: Close to 69A. When opening, lower surface: Close to 155A. Fully opened, upper surface: Towards the apex, close to 65B; towards the base, close to 60C; at base, close to 157B to 157C. Apices becoming closer to 56C with development. Fully opened, lower surface: Close to 56D.

*Sepals.*—Quantity/arrangement: About nine to ten in two whorls. Length: About 0.9 cm to 1.8 cm. Width: About 4 mm to 5 mm. Shape: Oblanceolate to ovate. Apex: Acute. Base: Truncate. Margin: Entire. Texture, upper and lower surfaces: Smooth, glabrous. Color, upper surface: Close to 146D. Color, lower surface: Close to 146A to 146B.

*Peduncles.*—Length: About 2.5 cm. Diameter: About 1.5 mm. Strength: Strong. Texture: Smooth, glabrous with silvery blue bloom. Color: Close to 189A.

*Reproductive organs.*—Stamens: Quantity: About 12 to 14 per flower. Filament length: About 1.8 cm. Filament color: Close to 155D. Anther length: About 3 mm. Anther shape: Oblong. Anther color: Close to 158B. Pollen amount: Scarce. Pollen color: Close to 196A. Pistils: Quantity: One per flower. Pistil length: About 3 cm. Stigma shape: Bi-parted and coiled at apices. Stigma color: Close to 155A. Style length: About 1.4 cm. Style color: Close to 155D. Ovary color: Close to 145A.

*Seeds/fruits.*—Seed and fruit development have not been observed.

Disease/pest resistance: Plants of the new *Dianthus* have not been observed to be resistant to pathogens and pests common to *Dianthus*.

Garden performance: Plants of the new *Dianthus* have been observed to have excellent garden performance and to tolerate wind, rain and temperatures ranging from about −5° C. to about 38° C.

It is claimed:

1. A new and distinct *Dianthus* plant named 'Heart's Desire' as illustrated and described.

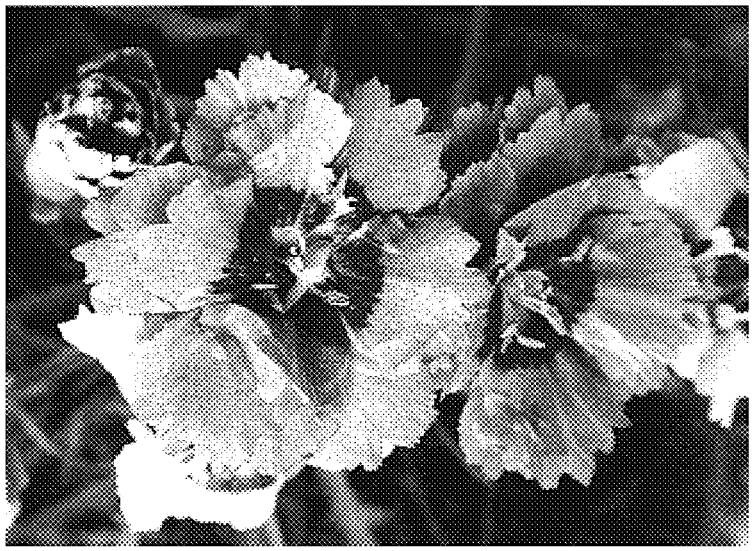
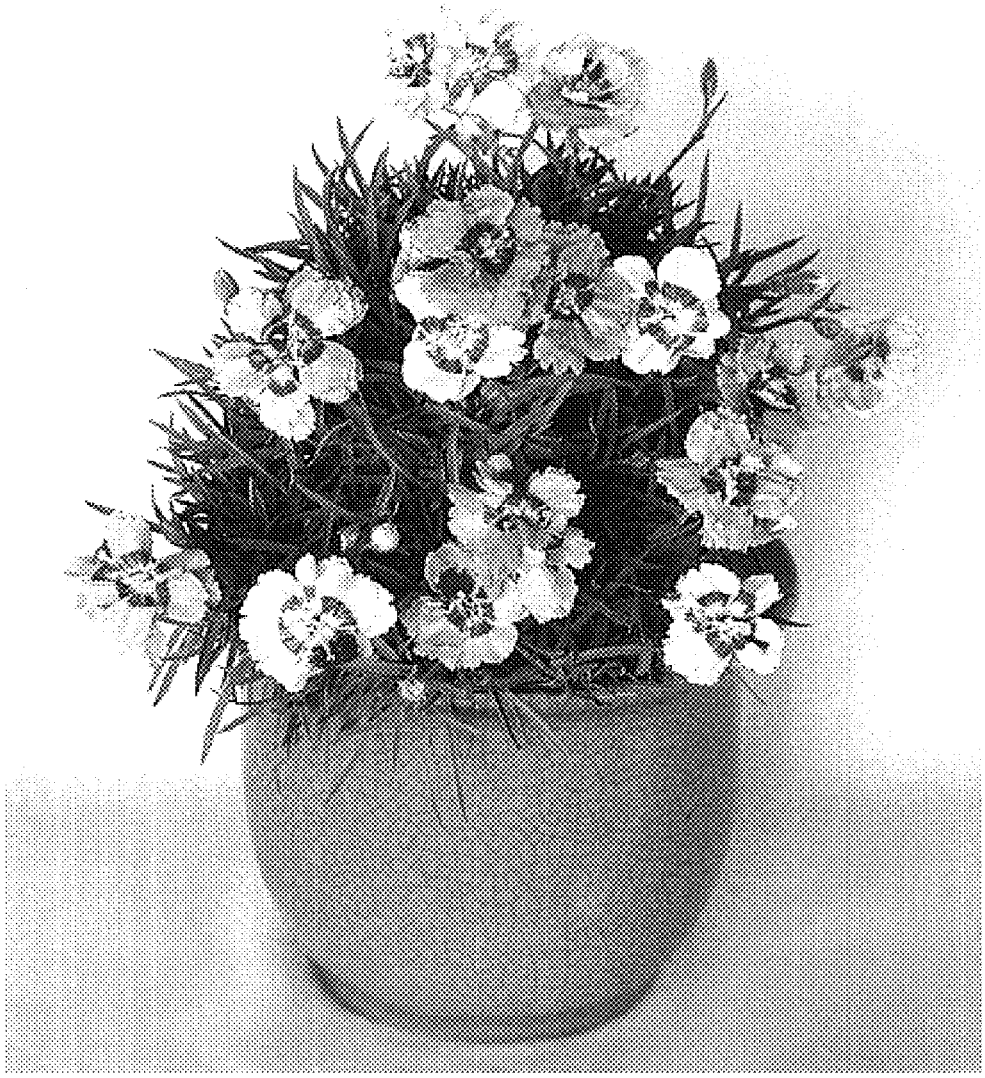

* * * * *